United States Patent [19]
Cesa et al.

[11] Patent Number: 4,937,380
[45] Date of Patent: Jun. 26, 1990

[54] 3-PENTENAMIDES FROM 1,3-BUTADIENES

[75] Inventors: Mark C. Cesa, South Euclid; Robert A. Dubbert, Solon; James D. Burrington, Richmond Heights, all of Ohio

[73] Assignee: The Standard Oil Company, Cleveland, Ohio

[21] Appl. No.: 918,653

[22] Filed: Oct. 14, 1986

Related U.S. Application Data

[63] Continuation of Ser. No. 685,561, Dec. 24, 1984, abandoned.

[51] Int. Cl.$^5$ ..................... C07C 102/00; C07B 43/06
[52] U.S. Cl. ..................................................... 564/132
[58] Field of Search ......................................... 564/132

[56] References Cited

U.S. PATENT DOCUMENTS

| 2,542,747 | 2/1951 | Barrick | 564/132 X |
| 2,542,766 | 2/1951 | Gresham | 564/132 |
| 3,168,553 | 2/1965 | Slaugh | 564/132 X |
| 3,523,971 | 8/1970 | Biale | 564/132 |
| 3,530,182 | 9/1970 | Haynes et al. | 564/132 |

Primary Examiner—Carolyn S. Elmore
Attorney, Agent, or Firm—C. S. Lynch; D. J. Untener; L. W. Evans

[57] ABSTRACT 1,3-butadienes are catalytically hydrocarbamylated to make 3-pentenamides.

8 Claims, No Drawings

3-PENTENAMIDES FROM 1,3-BUTADIENES

This application is a continuation of application Ser. No. 685,561 filed December 24, 1984, abandoned.

This invention relates to a new method of making 3-pentenamide or a substituted 3-pentenamide from 1,3-butadiene or a substituted 1,3-butadiene by hydrocarbamylation. Such a pentenamide is useful for making adipamide or a derivative thereof.

Adipamide is currently prepared from adiponitrile by controlled hydrolysis. The adiponitrile for the hydrolysis is prepared commercially by electrohydrodimerization of acrylonitrile or by hydrocyanation of 1,3-butadiene.

It is an object of the invention to provide a method of making 3-pentenamide or certain derivatives thereof.

It is a further object of the invention to convert a 1,3-butadiene to 3-pentenamide or a derivative thereof.

Another object is to provide a method of making a precursor for making adipamide, by the hydrocarbamylation of 1,3-butadiene.

Other objects, as well as aspects, features and advantages, of the invention will become apparent from a study of the specification, including the claims.

According to the present invention there is provided a process for making a compound of the formula

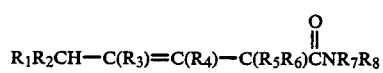 (1)

by providing an intimate liquid phase mixture comprising a compound of the formula

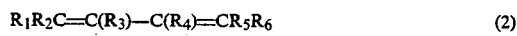 (2)

ammonia or an amine of the formula $R_7R_8NH$, CO and a catalytic material and allowing reaction to take place under essentially anhydrous conditions at a temperature in the range from 70° to 145° C., wherein each of $R_1$, $R_2$, $R_3$, $R_4$, $R_5$, $R_6$, $R_7$ and $R_8$ is selected independently from H and a $C_1$ to $C_{12}$ hydrocarbyl group containing no ethylenic or acetylenic unsaturation, wherein said catalytic material comprises a composition of the empirical formula

wherein M is one or more of Co, Mn, Rh, Ir, Fe, Ni, Re, Pt, Pd and Ru or is one or more of such metals plus H; L is one or more of $R_3P$, $R_3As$, and $R_3Bi$; X is one or more of F, Cl, Br and I; m is 1–16, n is 1–40, l is 0–40, x is 0–16 and $n+l+x \geq m$, where R is selected from alkyl, aryl, alkoxy, aryloxy, dialkylamido, diarylamido, alkylsulfido, and arylsulfido containing 1–30 carbon atoms, usually 1–12 carbon atoms, with the proviso that when M is Co, Rh, Ir or Ru no trivalent P, As or Bi ligand is present. Furthermore R is most often hydrocarbyl having 1–12 C atoms.

In U.S. Pat. No. 2,497,310 Larson discloses making amines by reacting $H_2$, CO, $NH_3$ and certain olefinic compounds including butadiene. In specific examples some amides are obtained from olefins in addition to amines when the temperature is well over 200° C. In any event the present method does not use $H_2$ as a reactant.

Especially useful catalysts herein are those wherein M is one or more of Mn, Co and Rh, with or without H.

In the usual practice of the invention the compound $R_7R_8NH$ is $NH_3$.

While not necessary, a solvent is usually used. The concentration of the conjugated diene may be as low as 0.01 weight percent in the mixture of diene plus solvent or as high as 100 weight percent (no solvent). Any non-interfering organic solvent which dissolves all reactants can be used. Examples are tetrahydrofuran, $CH_3CN$, dimethylformamide, benzene, toluene, hexane, pentane, xylene, diethyl ether, ethyl acetate, acetone, and methyl ethyl ketone.

By the term "catalytic material" as used herein and in the claims is meant a material present in the reaction mixture, which material is either a catalyst per se or is a precursor for the active catalyst which is formed within the reaction mixture.

In the present process the CO pressure is usually in the range from 100 to 50,000 psi. Lower pressures are expecially applicable, say from 100 to 2000 psi CO, when using a catalytic material wherein M is Rh.

The conjugated diene starting material of formula (2) that finds special application is 1,3-butadiene.

The 3-pentenamides herein are useful for making 1,4-hexanediamides. These can be converted to the corresponding diamines by known methods, and such diamines are useful to make nylon polyamide high polymer plastics by well known methods.

The 1,6-hexanediamides can be made from the 3-pentenamides herein by the hydrocarbamylation thereof. For instance, adipamide was made as follows:

A glass-lined stainless steel high pressure bomb reactor containing a magnetic stir bar was charged with 7.28 mole parts 3-pentenamide, 0.271 mole parts $Co_2(CO)_8$, 3.08 mole parts 4-methylpyridine, 2.8 mole parts triphenylphosphine, 52.9 mole parts $NH_3$ and 0.2 mole parts hexadecane internal standard in 195 mole parts of tetrahydrofuran solvent. Then CO was added to a pressure of 2200 psig, and the bomb was sealed and the reaction mixture stirred at 200° C. for 18 hours, then cooled to room temperature. The pressure was then released and the reaction mixture was analyzed and was found to contain adipamide. The other starting materials of formula (1) can be substituted in the foregoing procedure to make the corresponding diamides.

The following examples are merely illustrative and are not to be considered in any way limiting:

EXAMPLE 1

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 0.356 gram of $Mn_2(CO)_{10}$, and 0.1 gram of hydroquinone. The glass liner was placed in the high pressure reactor, the reactor was cooled to −78° C., and 53.6 mmole of 1,3-butadiene and 1.5 mL of $NH_3$ were condensed in. The reactor was pressurized at room temperature to 2500 psig with CO, sealed, and placed in a heating block maintained at 110° C. The reaction mixture was stirred at 110° C. for 25 hours. After this time the reactor was cooled to −78° C. and then the pressure was released. The liquid contents of the reactor were analyzed by gas chromatography, from which analysis it was determined that the conversion of butadiene was 55 percent and the yield of 3-pentenamide was 14.5 percent.

EXAMPLE 2

A glass liner for a 70 mL stainless steel high pressure reactor was equipped with a magnetic stir bar and charged under an argon atmophere with 15 mL of tetrahydrofuran, 0.2 mmol of hexadecane (internal standard,) 0.357 gram of $Mn_2(CO)_{10}$, and 0.1 gram of hydroquinone. The glass liner was placed in the high pressure reactor, the reactor was cooled to $-78°$ C., and 53.6 mmol of 1,3-butadiene and 1.5 mL of $NH_3$ were condensed in. The reactor was pressurized at room temperature to 2800 psig with CO, sealed, and placed in a heating block maintained at 120° C. The reaction mixture was stirred at 120° C. for 25 hours. After this time the reactor was cooled to $-78°$ C. and then the pressure was released. The liquid contents of the reactor were analyzed by gas chromatography, from which analysis it was determined that the conversion of butadiene was 68 percent and the yield of 3-pentenamide was 14.1 percent.

EXAMPLE 3

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 0.358 gram of $Mn_2(CO)_{10}$, and 0.1 gram of hydroquinone. The glass liner was placed in the high pressure reactor, the reactor was cooled to $-78°$ C., and 53.6 mmol of 1,3-butadiene and 1.5 mL of $NH_3$ were condensed in. The reactor was pressurized at room temperature to 3000 psig with CO, sealed, and placed in a heating block maintained at 80° C. The reaction mixture was stirred at 80° C. for 25 hours. After this time the reactor was cooled to $-78°$ C. and then the pressure was released. The liquid contents of the reactor were analyzed by gas chromotography, from which analysis it was determined that the conversion of butadiene was 38 percent and the yield of 3-pentenamide was 0.7 percent.

EXAMPLE 4

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 0.357 gram of $Mn_2(CO)_{10}$, and 0.1 gram of hydroquinone. The glass liner was placed in the high pressure reactor, the reactor was cooled to $-78°$ C., and 53.6 mmol of 1,3-butadiene and 1.5 mL of $NH_3$ were condensed in. The reactor was pressurized at room temperature to 2900 psig with CO, sealed, and placed in a heating block maintained at 100° C. The reaction mixture was stirred at 100° C. for 25 hours. After this time the reactor was cooled to $-78°$ C. and then the pressure was released. The liquid contents of the reactor were analyzed by gas chromatography, from which analysis it was determined that the conversion of butadiene was 60 percent and the yield of 3-pentenamide was 3 percent.

EXAMPLE 5

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 0.36 gram of $Mn_2(CO)_{10}$, and 0.1 gram of hydroquinone. The glass liner was placed in the high pressure reactor, the reactor was cooled to $-78°$ C., and 53.6 mmol of 1,3-butadiene and 1.5 mL of $NH_3$ were condensed in. The reactor was pressurized at room temperature to 2000 psig with CO, sealed, and placed in a heating block maintained at 150° C. The reaction mixture was stirred at 150° C. for 23 hours. After this time the reactor was cooled to $-78°$ C. and then the pressure was released. The liquid contents of the reactor were analyzed by gas chromatography, from which analysis it was determined that the yield of 3-pentenamide was 1.63 percent.

EXAMPLE 6

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 0.356 gram of $Mn_2(CO)_{10}$, 3.7 mmol of triphenylphosphine, and 0.1 gram of hydroquinone. The glass liner was placed in the high pressure reactor, the reactor was cooled to $-78°$ C., and 53.6 mmol of 1,3-butadiene and 1.5 mL of $NH_3$ were condensed in. The reactor was pressurized at room temperature to 1400 psig with CO, sealed, and placed in a heating block maintained at 110° C. The reaction mixture was stirred at 110° C. for 25 hours. After this time the reactor was cooled to $-78°$ C. and then the pressure was released. The liquid contents of the reactor were analyzed by gas chromatography, from which analysis it was determined that the conversion of butadiene was 51 percent and the yield of 3-pentenamide was 5.4 percent.

EXAMPLE 7

A glass liner for a 70 mL stainless steel high pressure reactor was equipped with a magnetic stir bar and charged under an argon atmosphere with 10 mL of tetrahydrofuran, 0.2 mmol of hexadecane (internal standard,) 0.79 mmol of $Co_2(CO)_8$, 3.08 mmol of 4-picoline, and 0.1 gram of hydroquinone. The glass liner was placed in the high pressure reactor, the reactor was cooled to $-78°$ C., and 123.9 mmol of 1,3-butadiene and 41.2 mmol of $NH_3$ were condensed in. The reactor was pressurized at room temperature to 1000 psig with CO, sealed, and placed in a heating block maintained at 120° C. The reaction mixture was stirred at 120° C. for 46.5 hours. After this time the rector was cooled to $-78°$ C. and then the pressure was released. The liquid contents of the reactor were analyzed by gas chromatography, from which analysis it was determined that the yield of 3-pentenamide was 0.9 percent.

EXAMPLE 8

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 149.1 mg of $[RhCl(CO)_2]_2$, and 0.1 gram of hydroquinone. The glass liner was placed in the high pressure reactor, the reactor was cooled to $-78°$ C., and 53.6 mmol of 1,3-butadiene and 0.3 mL of $NH_3$ were condensed in. The reactor was pressurized at room temperature to 700 psig with CO, sealed, and placed in a heating block maintained at 100° C. The reaction mixture was stirred at 100° C. for 24 hours. After this time the reactor was cooled to $-78°$ C. and then the pressure was released. The liquid contents of the reactor were analyzed by gas chromatography, from which analysis it was determined that the conversion of butadiene was 47 percent and the yield of 3-pentenamide was 15.4 percent based on $NH_3$ charged.

EXAMPLE 9

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 576.3 mg of $Rh_6(CO)_{16}$, and 0.1 gram of hydroquinone. The glass liner was placed in the high pressure reactor, the reactor was cooled to $-78°$ C., and 53.6 mmol of 1,3-butadiene and 0.3 mL of $NH_3$ were condensed in. The reactor was pressurized at room temperature to 100 psig with CO, sealed, and placed in a heating block maintained at 100° C. The reaction mixture was stirred at 100° C. for 24 hours. After this time the reactor was cooled to $-78°$ C. and then the pressure was released. The liquid contents of the reactor were analyzed by gas chromatography, from which analysis it was determined that the conversion of butadiene was 27 percent and the yield of 3-pentenamide was 1.8 percent based on $NH_3$ charged.

EXAMPLE 10

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 97.1 mg of $Rh_6(CO)_{16}$, and 0.1 gram of hydroquinone. The glass liner was placed in the high pressure reactor, the reactor was cooled to $-78°$ C., and 53.6 mmol of 1,3-butadiene and 0.3 mL of $NH_3$ were condensed in. The reactor was pressurized at room temperature to 300 psig with CO, sealed, and placed in a heating block maintained at 100° C. The reaction mixture was stirred at 100° C. for 24 hours. After this time the reactor was cooled to $-78°$ C. and then the pressure was released. The liquid contents of the reactor were analyzed by gas chromatography, from which analysis it was determined that the conversion of butadiene was 37 percent and the yield of 3-pentenamide was 3.2 percent based on $NH_3$ charged.

EXAMPLE 11

A glass liner for a 70 mL stainless steel high pressure reactor was equipped with a magnetic stir bar and charged under an argon atmosphere with 15 mL of tetrahydrofuran, 0.2 mmol of hexadecane (internal standard,) 98.0 mg of $Rh_6(CO)_{16}$, and 0.1 gram of hydroquinone. The glass liner was placed in the high pressure reactor, the reactor was cooled to $-78°$ C., and 53.6 mmol of 1,3-butadiene and 0.3 mL of $NH_3$ were condensed in. The reactor was pressurized at room temperature to 700 psig with CO, sealed, and placed in a heating block maintained at 100° C. The reaction mixture was stirred at 100° C. for 24 hours. After this time the reactor was cooled to $-78°$ C. and then the pressure was released. The liquid contents of the reactor were analyzed by gas chromatography, from which analysis it was determined that the conversion of butadiene was 57 percent and the yield of 3-pentenamide was 11 percent based on $NH_3$ charged.

EXAMPLE 12

Into a 70 mL volume glass-lined stainless steel high pressure bomb reactor containing a magnetic stir bar was charged at room temperature 15 mL tetrahydrofuran solvent, and 200 μL hexadecame internal standard. To this was added 0.6 mmol of $(\phi_3P)_2N^+Mn(CO)_5^-$ and about 0.66 mmol of $CF_3SO_3H$, which were allowed to react and were believed to form $HMn(CO)_5$, according to J. A. Gladysz et al., Inorganic Chemistry, 18, (4), 1163 (1979). The reactor was pressurized several times at about 500 psi and the pressure was released to flush out the air. After the last pressurization with CO the reactor was cooled to $-78°$ C. and the pressure then vented to atmospheric pressure. Then 53.6 mmol of 1,3-butadiene and about 65 mmol $NH_3$ were added and the reactor allowed to come to room temperature, and 2800 psig CO gas was added. The reactor was then placed in a heating block maintained at 140° C. The reaction mixture at this temperature had an initial pressure of 4400 psig. The reaction mixture was stirred at 140° C. for 24 hours. After this time the reactor was cooled to $-78°$ C. and then the pressure was released. The liquid contents of the reactor were analyzed by gas chromatography and mass spectroscopy, from which analyses it was determined that the conversion of butadiene was 84 percent and the yield of 3-pentenamide was 8.35 percent. The $(\phi_3P)_2N^-Mn(CO)_5^-$ was made by the procedure set forth in J. A. Gladysz et al., Inorganic Chemistry, 18, (3), 553 (1979).

EXAMPLE 13

A glass liner for a 70 mL stainless steel high pressure reactor was equipped with a magnetic stir bar and charged under an argon atmosphere with 15 mL of tetrahydrofuran, 0.34 mmol of hexadecane (internal standard,) 0.9 mmol of $Mn_2(CO)_{10}$, and 69 mmol of n-propylamine. The glass liner was placed in the high pressure reactor and the reactor was sealed. The reactor was cooled to $-78°$ C., and 4.0 mL of liquid 1,3-butadiene was condensed into the reactor. The reactor was pressurized to 1800 psig with CO at $-78°$ C. and allowed to warm to room temperature. The pressure at room temperature was 2800 psig. The reactor was heated to 110° C. and the contents were stirred at this temperature for 26 hours. The reactor was then cooled to $-78°$ C. and the pressure was released. The liquid contents of the reactor were analyzed by gas chromatography, and the major product was isolated by preparative gas chromatography and analyzed by $^1H$ nmr spectroscopy. The product N-n-propyl-3-pentenamide, was produced in approximately 25 percent yield, the conversion of butadiene was 81 percent.

EXAMPLE 14

A glass liner for a 70 mL stainless steel pressure reactor was equipped with a magnetic stir bar and charged under an argon atmosphere with 15 mL of tetrahydrofuran, 0.34 mmol of hexadecane (internal standard,) 0.92 mmol of $Mn_2(CO)_{10}$, and 53.6 mmol of isoprene. The glass liner was placed in the high pressure reactor and the reactor was sealed. The reactor was cooled to $-78°$ C., and 1.5 mL of liquid $NH_3$ was condensed into the reactor. The reactor was pressurized to 1800 psig with CO at $-78°$ C. and allowed to warm to room temperature. The pressure at room temperature was 2800 psig. The reactor was heated to 110° C. and the contents were stirred at this temperature for 26 hours. The reactor was then cooled to $-78°$ C. and the pressure was released. The liquid contents of the reactor were analyzed by gas chromatography, and the major product was isolated by preparative gas chromatography and analyzed by $^1H$ nmr spectroscopy. The product, 4- methyl-3-pentenamide, was produced in approximately 9 percent yield.

As will be evident to those skilled in the art, modifications of this invention can be made or followed in the light of the foregoing disclosure without departing from the spirit and scope of the disclosure or from the scope of the claims.

We claim:

1. A process for making a compound of the formula

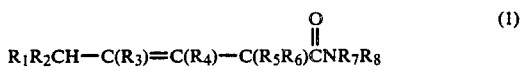

by providing an intimate liquid phase mixture comprising a compound of the formula

a compound of the formula $R_7R_8NH$, CO and a catalytic material and allowing reaction to take place under essentially anhydrous conditions at a temperature in the range from 70° to 14° C., wherein each of $R_1$, $R_2$, $R_3$, $R_4$, $R_5$, $R_6$, $R_7$ and $R_8$ is selected independently from H and a $C_1$ to $C_{12}$ hydrocarbyl group containing no ethylenic or acetylenic unsaturation, wherein said catalytic material comprises a composition of the empirical formula

wherein M is one or more of Co, Mn, Rh, Ir, Fe, Ni, Re, Pt, Pd and Ru or is one or more of such metals plus H; L is one or more of $R_3P$, $R_3As$, and $R_3Bi$; X is one or more of F, Cl, Br and I; m is 1-16, n is 1-40, l is 0-40, x is 0-16 and $n+1+x \geq m$, where R is selected from alkyl, aryl, alkoxy, aryloxy, dialkylamido, diarylamido, alkylsulfido, and arylsulfido containing 1-30 carbon atoms, with the proviso that when M is Co, Rh, Ir or Ru no trivalent P, As or Bi ligand is present.

2. A process of claim 1 wherein R contains 1-12 C atoms.

3. A process of claim 1 wherein R is hydrocarbyl and contains 1-12 C atoms.

4. A process of claim 2 wherein $R_7R_8NH$ is ammonia.

5. A process of claim 4 wherein compound (2) is 1,3-butadiene and compound (1) is 3-pentenamide.

6. A process of claim 1 wherein M is at least one of Co, Rh and Ru or is H and at least one of Co, Rh and Ru.

7. A process of claim 4 wherein M is at least one of Co, Rh and Ru or is H and at least one of Co, Rh and Ru.

8. A process of claim 5 wherein M is at least one of Co, Rh and Ru or is H and at least one of Co, Rh and Ru.

UNITED STATES PATENT AND TRADEMARK OFFICE
CERTIFICATE OF CORRECTION

PATENT NO. : 4,937,380

DATED : June 26, 1990

INVENTOR(S) : Cesa et al

It is certified that error appears in the above-identified patent and that said Letters Patent is hereby corrected as shown below:

Column 7, line 24, claim 1, line 10, change "14°C" to read ---145°C---.

Signed and Sealed this

Twentieth Day of August, 1991

Attest:

HARRY F. MANBECK, JR.

Attesting Officer

Commissioner of Patents and Trademarks